(12) United States Patent
Kim et al.

(10) Patent No.: US 7,718,420 B2
(45) Date of Patent: May 18, 2010

(54) MICROFLUIDIC BIOCHIP FOR BLOOD TYPING BASED ON AGGLUTINATION REACTION

(75) Inventors: Dong-Sung Kim, Pohang (KR);
Tai-Hun Kwon, Pohang (KR)

(73) Assignee: Postech Academy-Industry Foundation, Pohang (KR)

( * ) Notice: Subject to any disclaimer, the term of this patent is extended or adjusted under 35 U.S.C. 154(b) by 76 days.

(21) Appl. No.: 11/697,140

(22) Filed: Apr. 5, 2007

(65) Prior Publication Data

US 2008/0085551 A1     Apr. 10, 2008

Related U.S. Application Data

(60) Provisional application No. 60/850,489, filed on Oct. 10, 2006.

(51) Int. Cl.
*C12M 3/00* (2006.01)
(52) U.S. Cl. .................................................. 435/287.3
(58) Field of Classification Search ....................... None
See application file for complete search history.

(56) References Cited

U.S. PATENT DOCUMENTS

| | | | |
|---|---|---|---|
| 6,699,384 B1 * | 3/2004 | Lin et al. | 205/792 |
| 7,223,363 B2 * | 5/2007 | McNeely et al. | 422/58 |
| 7,442,556 B2 * | 10/2008 | Manger et al. | 436/180 |
| 2007/0037172 A1 * | 2/2007 | Chiu et al. | 435/6 |

OTHER PUBLICATIONS

Microsystems and BioMEMS Lab, University of Cincinnati, "A Disposable Plastic Lab-on-a-chip for Blood Typing Fabricated by Microinjection Molding," The 8th Korean MEMS Conference, Jeju, Apr. 6-8, 2006.
Kim et al., "Disposable integrated microfluidic biochip for blood typing by plastic microinjection moulding," Lab Chip, 2006, vol. 7 pp. 794-802.

* cited by examiner

*Primary Examiner*—Ann Y Lam
(74) *Attorney, Agent, or Firm*—Marshall, Gerstein & Borun LLP

(57) ABSTRACT

The present invention is directed to a microfluidic biochip based on an agglutination reaction that is frequently used in qualitative typing in the diagnostic medicine field by realizing a specimen inlet, a reagent inlet, a split microchannel, transfer microchannels, a chaos micromixer, a reaction microchamber, a microfilter, a passive microvalve, and an outlet on a plastic microchip. Particularly, the biochip of the present invention is characterized in that portability thereof is superior and a small amount (about 1 µl) of each of a specimen and a reagent is used. In addition, the biochip of the present invention can be cheaply made through conventional photolithography, electroplating, injection molding, and bonding. Therefore, by utilizing the microfluidic biochip for blood typing according to the present invention, a point-of-care diagnosis for performing blood typing based on an agglutination reaction at any place becomes possible.

34 Claims, 11 Drawing Sheets
(4 of 11 Drawing Sheet(s) Filed in Color)

MICROFLUIDIC BIOCHIP FOR BLOOD TYPING BASED ON AGGLUTINATION REACTION

CROSS-REFERENCE TO RELATED APPLICATION

This application claims priority to and the benefit of U.S. Application No. 60/850,489 filed on Oct. 10, 2006, the entire contents of which are incorporated herein by reference.

BACKGROUND OF THE INVENTION

1. Field of the Invention

The present invention relates to a point-of-care microfluidic biochip that can be used to directly perform blood typing at any place, and to a method of manufacturing the point-of-care microfluidic biochip.

2. Description of the Related Art

When a blood transfusion is necessary, blood typing for both a blood recipient and a blood donor is absolutely necessary to prevent a transfusion-caused accident. Blood typing before a blood transfusion involves performing ABO blood typing and Rh(D) blood typing, after which crossmatching is performed. Particularly, agglutinins present in serums of the ABO blood system among a variety of blood types induce hemolysis in a blood vessel by fixing unfitted red blood cells. This may result in death of a patient (blood recipient). Therefore, accurate blood typing is absolutely necessary.

Blood typing is generally performed by identifying an agglutination reaction of a red blood cell and a serum and determining that the agglutinogen corresponding to an agglutinin of the serum exists in the red blood cell. That is, when the red blood cell of a specimen reacts with an Anti-A serum to induce agglutination but does not react with an Anti-B serum, it can be determined that the red blood cell of the specimen has only agglutinogen for type-A and thus the red blood cell of the specimen can be determined as type-A. In order to perform more accurate blood typing, red cell typing (i.e., forward typing) and serum typing (i.e., backward typing) are performed. By simultaneously performing these two forms of typing, the typing results can be compared with each other and thus the reliability of the blood typing increases and a weak antigen blood type that may exist in the specimen can be detected.

Weak antigen blood types (e.g., A2, A3, Aint, and the like) exist in type-A blood and weak antigen blood types (e.g., B3, Bint, and the like) exist in type-B blood. Since the weak antigen blood types tend to be weak in agglutination reaction with the corresponding serum, the chance of mis-blood typing to type-O is high. Therefore, in order to more accurately perform blood typing, it is absolutely necessary to effectively mix red blood cells with serum. In order to improve the reliability of blood typing, it is also absolutely necessary to simultaneously perform red cell typing and serum typing.

The following conventional blood typing methods and systems are well known: plate typing, gel card typing, automatic blood typing systems, a recently represented micro-blood-typing system (S.-J. Lee, H.-W. Kang, Y. Kim, G.-W. Lee, G. Lim and D.-W. Cho, "Development of a Micro-Blood-Typing System Using Micro-Stereolithography," Sensors and Materials, Vol. 17, pp. 113-123, 2005), and a blood typing system using a microchannel and a microfilter (Korean Patent No. 0520896).

In the case of plate typing, a specimen and a reagent are put on a plate, such as a slide glass, and mixed with each other, and after a predetermined reaction time has elapsed, it is determined if agglutination occurs. Most of the processes for plate typing are manually performed. However, due to such manual performing of the processes for plate typing, the determination of whether agglutination occurs is dependent upon a tester's subjective assessment. Thus, the typing result lacks objectivity. Further, since the specimen is manually manipulated, the tester may be at risk of infection from the specimen.

Recently, with the push toward greater automation in all aspects of diagnostic medicine, a variety of automation systems for diagnostic tests have been developed and proposed. Among these systems, the gel card typing method is known as a semiautomatic typing method that gives accurate typing results. However, the gel card typing method requires expensive supplies and testers who can manipulate a machine such as a centrifuge. In addition, since the sinking of blood takes a lot of time, the gel card typing method is time-consuming, thereby making it difficult to apply this method in an emergency.

The automatic blood typing system actually provides for fully automatic blood typing. However, the automatic blood typing system is very expensive and large in its equipment size. Hence, only large hospitals such as blood banks can utilize the automatic blood typing system.

Accordingly, Lee et al. have proposed a down-sized blood typing system in which a flow split channel, a chaos micromixer, and a reaction chamber are integrated through microstereolithography. The down-sized blood typing system splits injected blood through a flow split channel and, at the same time, mixes the blood with a reagent, after which it is determined if blood cell agglutination occurs in a reaction chamber. The down-sized blood typing system is easy to carry and may be used in dealing with emergency situations. However, a drawback of the system is that it is time-consuming to manufacture the same using the micro-stereolithography. Also, the cost of manufacturing the system is high.

Finally, all of the conventional semiautomatic or fully automatic blood typing methods need about 20 µl of the specimen for blood typing. When compared with the manual bloody typing method, there is no difference in the amount of required specimen between the manual blood typing method and the fully automatic (or semiautomatic) blood typing method. In addition, there still remains the inconvenience with respect to the need to perform repeated collection of specimens.

Korean Patent No. 0520896 discloses a blood typing system using a microchannel and a microfilter. This blood typing system uses a method in which a specimen is split through the microchannel and reacts with a reagent in a reagent storing chamber, and agglutinated blood is filtered off through the microfilter. Further, this blood typing system uses a relatively small amount (10 µl or less) of the specimen. However, this blood typing system is configured to induce natural mixing and reaction between the specimen and the reagent in the micro-chamber. As described above, effective mixing of the specimen and the reagent is essential in order to detect an unexpected antibody that may exist in the blood cell. With the use of such a fine channel or micro channel, however, only a mixing effect by diffusion can be expected due to a reduction in a characteristic length, while a mixing effect by turbulence cannot be expected. Therefore, mixing performance is significantly deteriorated. For example, several hours are necessary for the natural mixture by diffusion in a microchannel having a width of 100 µm. Therefore, the micro blood typing system not having a mixing apparatus is limited in performance. Furthermore, in this blood typing system, the microfilter is formed in a cylindrical shape having a uniform thickness in a lengthwise direction. However, the thickness of the microfilter is too small to be mass-produced through, for example, an injection molding process. Finally, the blood typing system disclosed in Korean Patent No. 0520896 uses specific, preset reagents and is designed to perform a blood cell test. Thus, this blood typing system has limitations with respect to accurately performing blood typing.

Therefore, there is a need to develop an agglutination test system for diagnostic medicine, that, in a single apparatus, can perform a reaction between a specimen and a reagent and read if agglutination occurs while using a relatively small amount of each of the specimen and the reagent, thereby enabling (i) an objective diagnosis of the agglutination test for blood typing, (ii) preservation of the agglutination test result, (iii) cheap manufacture, and (iv) point-of-care resulting from easy portability.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a point-of-care microfluidic biochip having the advantages of using a relatively small amount of each of a specimen and a reagent, effectively mixing the specimen and the reagent, and enabling objective blood typing by allowing both reaction and reading to determine if agglutination occurs to be performed thereon.

Exemplary embodiments of the present invention also provide a biochip that can be cheaply made of plastic through a mass-production process, such as an injection molding process.

Exemplary embodiments of the present invention also provide a biochip that is easy to carry and thus enables a point-of-care diagnosis and preservation of an agglutination result.

Resultantly, exemplary embodiments of the present invention provide a point-of-care microfluidic biochip that is formed of plastic, on or in which there are formed a specimen inlet, a reagent inlet, a microchannel system for split and flow of the specimen and the reagent, a micromixer for effectively mixing the specimen with the reagent, a reaction microchamber for reaction between the specimen and the reagent, a multi-step microfilter for detecting a reacted test sample and reagent, a passive microvalve for controlling flows of the specimen and the reagent, and an outlet, thereby allowing for blood typing to be simply performed based on an agglutination test of diagnostic medicine.

Exemplary embodiments of the present invention provide a microfluidic biochip for blood typing based on an agglutination reaction, including i) a specimen transfer microchannel provided with a specimen inlet, ii) one or more reagent transfer microchannels provided with a reagent inlet, iii) one or more micromixers for mixing a specimen and a reagent, which are flowing along thereof, with each other, the micromixer being connected to downstream ends of the specimen and reagent transfer microchannels, iv) a first passive microvalve for controlling a flow of the specimen and the reagent, the first passive microvalve being formed between the downstream ends of the specimen and reagent transfer microchannels and an upstream end of the micromixer, v) a reaction microchamber for inducing the reaction between the specimen and the reagent that are mixed with each other and stored therein, the reaction microchamber being connected to a downstream end of the micromixer, vi) a microfilter for filtering off a agglutination body resulting from the agglutination reaction between the specimen and the reagent, the microfilter being connected to a downstream end of the microchamber, vii) a second passive microvalve for controlling the specimen and the reagent that are mixed with each other to stay at the reaction microchamber, the second passive microvalve being formed between the downstream end of the microchamber and an upstream end of the microfilter, and viii) an outlet for discharging the specimen and the reagent that are used for the blood typing, the outlet being connected to a downstream end of the microfilter.

The microfilter may include a plurality of micropillars arranged in a plurality of columns arranged at periodic intervals in a direction in which fluid flows, and filter spaces formed respectively between pairs of the micropillars of adjacent columns, and each of the filter spaces may have an inlet that is wider than an outlet.

The columns in which the micropillars are arranged may be arranged to be uniformly spaced apart from each other.

An initial section of the microfilter may have sections where the filter spaces of the columns are reduced in multiple steps in a fluid flow direction.

The initial section of the microfilter may have sections where sizes of the micropillars of the columns increase in multiple steps.

The initial section of the microfilter may have sections where the number of the micropillars in the columns increases in multiple steps.

Each of the micropillars may have a surface that is located at a downstream side with respect to the fluid flow direction and that is larger than a surface that is located at an upstream side with respect to the fluid flow direction.

A planar cross-section of each of the micropillars may be formed in a trapezoidal shape or a pentagonal shape.

The first passive microvalve may be shaped such that a width thereof is sharply reduced from the reagent transfer microchannel or the specimen transfer microchannel, and also the second passive microvalve may be shaped such that a width thereof is sharply reduced from the reaction microchamber.

A plurality of passages may be branched off from the specimen transfer microchannel and respectively connected to the micromixers to split the injected specimen and transfer the split specimens to the micromixers.

The reagent transfer microchannels may be respectively connected to the micromixers, each of the reagent transfer microchannels being provided with an independent reagent inlet so that different types of the reagents can be injected through the independent reagent inlets.

The micromixer transfers the specimen and the reagent through a three-dimensional serpentine passage such that the specimen and the reagent are mixed with each other by a combination of a split/recombine chaotic mixture mechanism and a chaotic mixture mechanism of chaotic advection.

The micromixer may includes an inflow channel through which the specimen and the reagent are joined together, the inflow channel being provided with a pair of inlets through which the specimen and the reagent are respectively injected; an outflow channel through which the specimen and the reagent are mixed with each other and discharged; and first and second mixing units that are disposed in a row and connected between the inflow and outflow channels to mix the specimen and the reagent with each other.

In the micromixer, the first mixing unit may include a pair of first split channels branched off from the inflow channel and a first combine channel communicating with each end of the first split channels, the first split channels extending toward a first side with respect to a fluid flow direction in the inflow channel so that the mixture fluid of the specimen and the reagent that are combined with each other at the inflow channel is split again and passes therethrough, the first combine channel being disposed on a different layer from the first split channels; the second mixing unit may include a pair of split channels branched off from the first combine channel and a second combine channel communicating with each end of the second split channels, the second combine channel being disposed on a different layer from the second split channels, the mixture fluids split through the second split channels being combined and pass through the second combine channel; and the secondary combine channel may extend to the discharge channel.

Each of the first split channels may be divided into a main channel extending parallel to the inflow channel and a branch channel extending from the main channel toward the first side in a direction substantially perpendicular to the fluid flow direction in the main channel.

Each of the second split channels may include a main channel extending parallel to the inflow channel and a branch channel extending from the main channel toward the second side in a direction substantially perpendicular to the fluid flow direction in the main channel.

The first and second mixing units that are disposed in a row may be repeated several times.

The first split channels of the first mixing unit may be formed on a different layer from the second split channels of the second mixing unit, and the first combine channel of the first mixing unit is formed on a different layer from the second combine channel of the second mixing unit.

The first combine channel may be formed on the same layer as the second split channels.

The first and second split channels and the first and second combine channels may be formed such that the mixture fluid split through each of the split channels can move by a substantially identical distance while the mixture fluid is transferred to a recombine point through each of the combine channels.

The specimen may be red blood cells of a blood sample and the reagent may be a standard serum. Alternatively, the specimen may be a serum of a blood sample and the reagent may be standard red blood cells.

In other exemplary embodiments of the present invention, a method of manufacturing the above-described microfluidic biochip includes i) preparing a substrate including a first groove having a shape corresponding to all of the specimen and reagent channels, a first layer portion of the micromixer, the first and second passive microvalves, a first layer portion of the reaction microchamber, and the microfilter, ii) preparing a second substrate including a second groove having a shape corresponding to all of a second layer portion of the micromixer and a second layer portion of the reaction microchamber, and iii) bonding the first and second substrates together.

BRIEF DESCRIPTION OF THE DRAWINGS

The application file contains four drawings executed in color (FIGS. 7 and 8A-8C). Copies of this patent application publication with color drawings will be provided by the Office upon request and payment of the necessary fee.

DETAILED DESCRIPTION OF THE EMBODIMENTS

The present invention will now be described more fully with reference to the accompanying drawings, in which exemplary embodiments of the invention are shown. The invention may, however, be embodied in many different forms and should not be construed as being limited to the exemplary embodiments set forth herein; rather, these embodiments are provided so that this disclosure will be thorough and complete, and will fully convey the concept of the invention to those skilled in the art. In the accompanying drawings, a description of parts that are not related to the present invention is omitted for the simplicity and the same reference numbers will be used to refer to the same or like parts.

Figure 1:
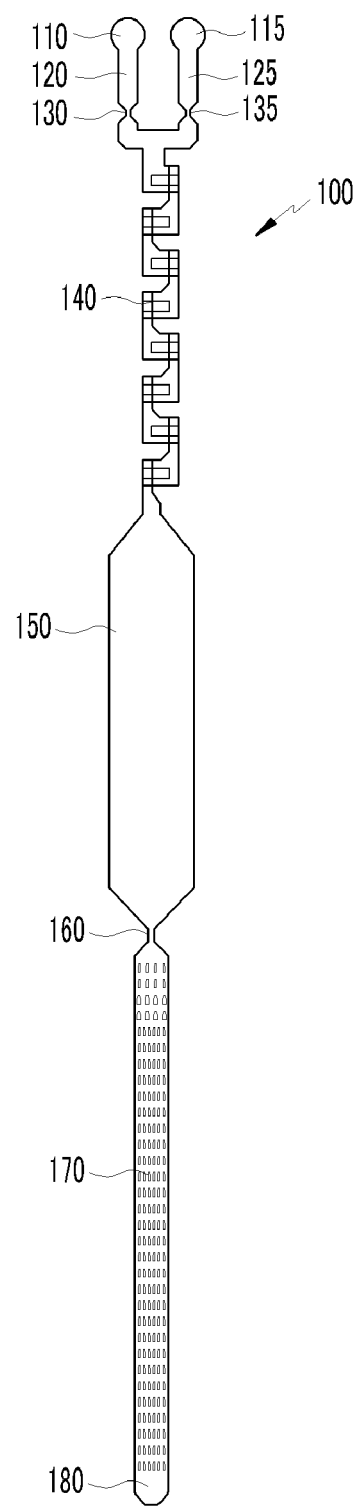
FIG. 1 is a top plan view of a basic structure of a microfluidic biochip for blood typing according to a first exemplary embodiment of the present invention.

First, the following will describe a basic structure of a point-of-care microfluidic biochip for blood typing based on an agglutination reaction according to the present invention with reference to FIG. 1. FIG. 1 is a top plan view of a basic structure of a microfluidic biochip for blood typing according to a first exemplary embodiment of the present invention.

Referring to FIG. 1, a microfluidic biochip 100 for blood typing according to the first exemplary embodiment of the present invention includes a specimen inlet 110, a reagent inlet 115, microchannels 120 and 125 for respectively transferring a specimen and a reagent, first passive microvalves 130 and 135 for respectively controlling the flow of the specimen and the reagent, a chaos micromixer 140 for effectively mixing the specimen with the reagent, a reaction microchamber 150 for inducing reaction by storing a mixture of the specimen and the reagent, a second passive microvalve 160 for allowing the mixture of the specimen and the reagent to stay in the reaction microchamber 150, a microfilter 170 for filtering off a red blood cell agglutination body formed by an agglutination reaction of the specimen and the reagent that are mixed with each other, and an outlet 180 for discharging the specimen and the reagent that are used for blood typing.

According to red cell typing (forward typing), blood typing is performed by determining that agglutinogen corresponding to a reference serum such as Anti-A, Anti-B, Anti-AB, Anti-A1, Anti-H, and Anti-D exists in a red blood cell when the red blood cell of the specimen induces agglutination with the standard serum. For example, it can be determined that a red blood cell that induces an agglutination reaction with Anti-A has a type-A agglutinogen (blood type A or blood type AB). Therefore, for red cell typing, the specimen is the red blood cell of the blood sample and the reagent is the standard serum.

According to serum typing (backward typing), blood typing is performed by determining that an agglutinin corresponding to a test red blood cell such as Test cell A1, Test cell A2, Test cell B, and Test cell O exists in serum when the serum of the specimen induces an agglutination reaction with a standard red blood cell. For example, it can be determined that serum that induces an agglutination reaction with Test A has a type-A agglutinin (blood type A or blood type AB). Therefore, for serum typing, the specimen is the serum of the blood sample and the reagent is the standard red blood cell.

For each form of typing, the specimen and the reagent are respectively injected through the specimen inlet 110 and the reagent inlet 115. An amount of each of the specimen and the reagent injected is about 3 μl. Specifically, since the specimen inlet 110 and the reagent inlet 115 are separately provided, it becomes possible to use a variety of different types of reagents that can be used for serum typing and red cell typing. The injected specimen and reagent are respectively directed to the first passive microvalves 130 and 135 via the respective microchannels 120 and 125 by a driving force generated by an external pressure-transferring device such as a needle pump, by surface tension, by gravity generated and intensified by shaking the chip, or the like.

The first passive microvalves 130 and 135 are shaped such that widths thereof are sharply reduced. This shape leads to a sudden variation in surface tension and thus induces an effect where the flows of the specimen and reagent stop at the respective first passive microvalves 130 and 135. Specifically, the surface tension effect of the first passive microvalves 130 and 135 may be enhanced as the surfaces thereof are formed to be hydrophobic or hydrophilic according to a plastic surface property. The first passive microvalves 130 and 135 function to allow the specimen and reagent to be simultaneously directed to the chaos micromixer 140 and effectively mixed. That is, the specimen and reagent stopped at the first passive microvalves 130 and 135 are further directed to the chaos micromixer 140 by a driving force generated by an external pressure-transferring device such as a needle pump, by surface tension, by gravity generated and intensified by shaking the chip, or the like, and are effectively mixed with each other.

Specifically, the chaos micromixer 140 is a spiral lamination chaos mixer in which F-shaped mixture units are arranged in a predetermined pattern on upper and lower plates, such that a split/recombine chaotic mixture mechanism and a chaotic mixture mechanism of chaotic advection are effectively combined with each other. Hence, the specimen is effectively mixed with the reagent. Such effective mixing superbly increases blood typing performance and helps to effectively detect an unexpected blood type that may exist in the specimen. Further, the spiral lamination chaos micromixer 140 is simple in shape and thus can be manufactured through a mass-production process. The specimen and the reagent that are mixed with each other by the spiral lamination chaos micromixer 140 are further directed to the reaction microchamber 150 by a driving force generated by an external pressure-transferring device such as a needle pump, by surface tension, by gravity generated and intensified by shaking the chip, or the like.

As with the spiral lamination chaos micromixer 140, the reaction microchamber 150 is patterned on upper and lower plates to thereby increase a volume of the chamber. The mixture of the specimen and reagent is held in the reaction microchamber 150 by the second passive microvalve 160 for a reaction time (about 1-3 minutes) during which the specimen and the reagent react with each other. At this point, if an agglutinogen and an agglutinin exist respectively in the specimen and the reagent, the agglutination reaction occurs between the red blood cells.

As with the first passive microvalves 130 and 135, the second passive microvalve 160 is also shaped such that a width thereof is sharply reduced. This shape leads to a sudden variation in surface tension and thus induces an effect where the flow of the mixture of the specimen and reagent stops at the second passive microvalve 160. Specifically, the surface tension effect of the second passive microvalve 160 may be enhanced as the surfaces thereof is formed to be hydrophobic or hydrophilic according to a plastic surface property. After a predetermined reaction time (about 1-3 minutes) during which the specimen and the reagent react with each other has elapsed, the mixture of the specimen and the regent is directed to the microfilter 170 by a driving force generated by an external pressure-transferring device such as a needle pump, by surface tension, by gravity generated and intensified by shaking the chip, or the like.

The microfilter 170 provided in the microfluidic biochip 100 for blood typing of the present exemplary embodiment has a filter space that is reduced in multiple steps to effectively filter off the agglutinated red blood cells for which the agglutination reaction is induced. Specifically, the filter space is larger than the size of a normal red blood cell and thus the red blood cells for which no agglutination reaction occurs can easily pass through the microfilter 170. However, agglutinated red blood cells whose size increases due to the agglutination reaction are easily filtered off by the microfilter 170.

Finally, the specimen and the reagent that react with each other for a predetermined reaction time pass through the microfilter 170 and are discharged through the outlet 180. At this point, when the agglutination reaction occurs between the specimen and the reagent, the agglutinated red blood cells are filtered off by the microfilter 170. When no agglutination reaction occurs, the red blood cells pass through the microfilter 170. Thus, it is easily determined by the naked eye if agglutination occurs, and blood typing is made possible based on such a process.

Figure 2A:
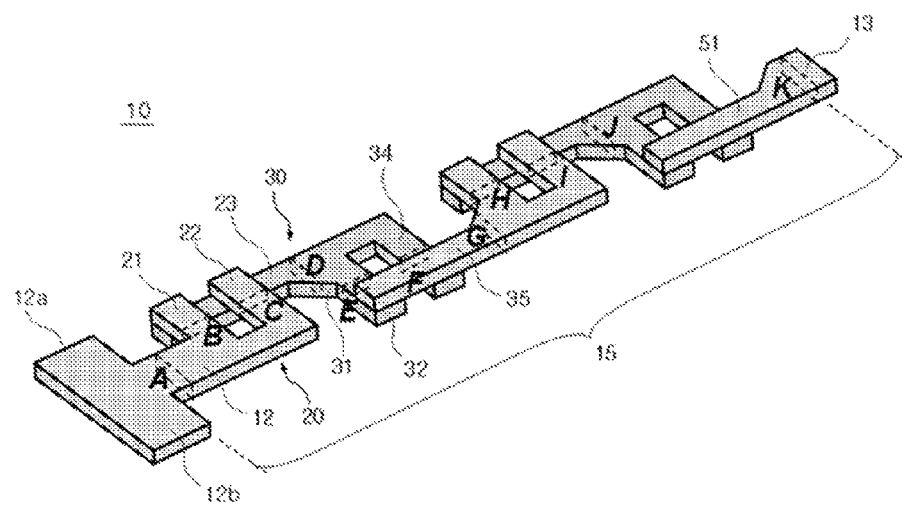
FIG. 2A is a perspective view for describing a concept of a micromixer of a microfluidic biochip for blood typing according to the first embodiment of the present invention.
Figure 2B:
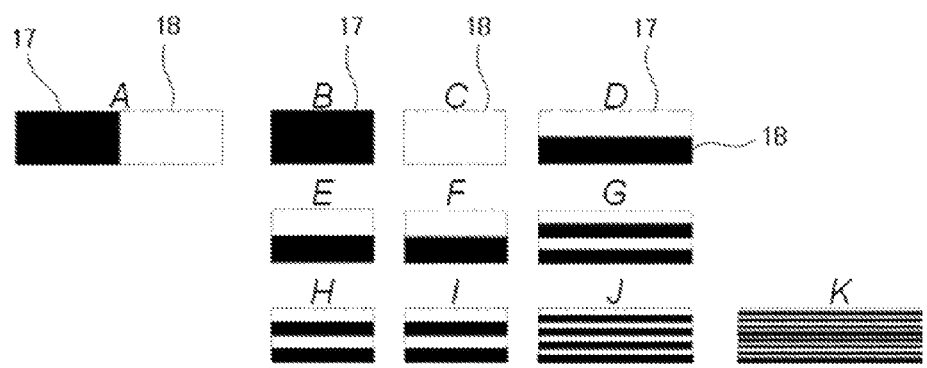
FIG. 2B is a schematic view illustrating a sectional mixture movement occurring at a location indicated in FIG. 2A.

The following will describe the basic concept involved in the structure and mixture of the micromixer of the microfluidic biochip for blood typing of the first exemplary embodiment with reference to FIGS. 2A and 2B. FIG. 2A is a perspective view for describing a concept of the micromixer of the microfluidic biochip for blood typing according to the first embodiment of the present invention, and FIG. 2B is a schematic view illustrating a sectional mixture movement occurring at a location indicated in FIG. 2A.

The micromixer 10 according to the present exemplary embodiment includes a pair of inlets 12a and 12b through which two different fluids (i.e., the specimen and the reagent) are introduced, an inflow channel 12 through which the specimen and the reagent join each other and pass, an outflow channel 13 through which the specimen and the reagent are mixed and discharged, and a mixing portion 15 that is formed and connected between the inflow channel 12 and the outflow channel 13 to mix the specimen and the reagent with each other. The mixing portion 15 includes first and second mixing units 20 and 30 that are disposed in a row.

The first mixing unit 20 includes a pair of first split channels 21 and 22 branched off from the inflow channel 12 and a first combine channel 23 communicating with each end of the first split channels 21 and 22. The first split channels 21 and 22 extend toward a first side with respect to a fluid flow direction in the inflow channel 12 so that the mixture fluid of the specimen and the reagent that are combined with each other at the inflow channel 12 is split again and passes therethrough. The first combine channel 23 is disposed on a different layer from the first split channels 21 and 22. The mixture fluids split through the first split channels 21 and 22 are combined and pass through the first combine channel 23.

The second mixing unit 30 includes a pair of split channels 32 and 34 branched off from the first combine channel 23 and a second combine channel 35 communicating with each end of the second split channels 32 and 34. The second split channels 32 and 34 extend toward a second side opposite to the first side. The mixture fluid of the specimen and the reagent that are combined with each other at the first combine channel 23 is split again and passes through the second split channels 32 and 34. The second combine channel 35 is disposed on a different layer from the second split channels 32 and 34. The mixture fluids split through the second split channels 32 and 34 are combined and pass through the second combine channel 35.

In the present exemplary embodiment, the first split channels 21 and 22 extend leftward with respect to the fluid flow direction in the inflow channel 12 and the second split channels 32 and 34 extend rightward with respect to the fluid flow direction in the inflow channel 12. Further, the first split channels 21 and 22 extend in a direction substantially perpendicular to the fluid flow direction in the inflow channel 12. Likewise, the second split channels 32 and 34 extend in a direction substantially perpendicular to the fluid flow direction in the inflow channel 12. However, the present invention is not limited to the above configuration. For example, the first split channels 21 and 22 may extend rightward while the second split channels 32 and 34 may extend leftward.

Each of the first split channels 21 and 22 may be divided into a main channel extending parallel to the inflow channel 12 and a branch channel extending from the main channel toward the first side in a direction substantially perpendicular to the fluid flow direction in the main channel. By the pair of branch channels, the split channels are formed in an F-shape. When the number of the split channels increases, a length of the main channel increases and the number of the branch channels increases. As with the first split channels 21 and 22, each of the second split channels 32 and 34 may be divided into a main channel extending parallel to the inflow channel 12 and a branch channel extending from the main channel toward the second side in a direction substantially perpendicular to the fluid flow direction in the main channel.

In the mixing portion 15, the structure of the successively disposed first and second mixing units 20 and 30 may be repeated several times. In the mixing portion 15 shown in FIG. 2A, the successive arrangement of the first and second mixing units 20 and 30 is repeated two times before the mixing portion 15 reaches the outflow channel 13. A final combine channel 51 is connected to the outflow channel 13 to discharge the specimen and reagent that are evenly mixed with each other.

Meanwhile, in the mixing units that are successively disposed, the split channels are disposed on a different layer from the combine channels. That is, the first split channels 21 and 22 of the first mixing unit 20 are formed on a different layer from the second split channels 32 and 34 of the second mixing unit 30. Also, the first combine channel 23 of the first mixing unit 20 is formed on a different layer from the second combine channel 35 of the second mixing unit 30. The first combine channel 23 is formed on the same layer as the second split channels 32 and 34 and connected to the second split channels 32 and 34. The second combine channel 35 is formed on the same layer as the first split channels 21 and 22. By the above-described first and second mixing units 20 and 30, a three-dimensional serpentine fluid passage is formed. The specimen and the reagent are transferred through the three-dimensional serpentine fluid passage, during the course of which the specimen and reagent are evenly mixed with each other as a split-recombine chaotic mixture mechanism is used in combination with a chaotic mixture mechanism of chaotic advection.

The first and second split channels 21, 22, 32, and 34 and the first and second combine channels 23 and 35 are formed such that the mixture fluid split through each of the split channels can move by a substantially identical distance while the mixture fluid is transferred to a recombine point through each of the combine channels.

Further, a widened portion 31 is formed at a start point where the second split channels 32 and 34 are branched off from the first combine channel 23, thereby allowing the mixture fluid to effectively flow.

The following will describe a process for splitting the injected mixture fluid with reference to FIG. 2B.

When the fluid flow of the specimen and the reagent that are injected through the respective inlets 12a and 12b and combined at the inflow channel 12 meets the first mixing unit 20, the fluid flow is split into two fluid flows through the first split channels 21 and 22 and recombined at the first combine channel 23. That is, the specimen 17 and the reagent 18 that are respectively injected through the inlets 12a and 12b are combined at a section A of FIG. 2A, as shown by A of FIG. 2B, and split at the first split channels 21 and 22, as shown by B and C of FIG. 2B. Due to the arrangement of the first mixing unit 20 according to the present exemplary embodiment, the split specimen 17 and reagent 18 are combined in a thickness direction such that the recombination thereof is realized as a layered configuration as shown by D of FIG. 2B. By this mixture mechanism, layering in the thickness direction at D, G, J, and K of FIG. 2A is realized and thus the number of boundary surfaces of the fluids increases exponentially, thereby inducing chaotic mixing.

According to research performed by Schönfeld et al. (F. Schönfeld, V. Hessel and C. Hofmann, "An Optimized Split-and-Recombine Micro-mixer with Uniform 'Chaotic' Mixing," Lab on a Chip, vol. 4, pp. 65-69, 2004), when there is no split wall in the recombining section, it is difficult to expect the ideal layering of FIG. 2B. However, since the micromixer 10 according to the present exemplary embodiment has a 3-dimensional serpentine shape, chaotic advection is induced when the fluid flows toward the outflow channel 13 of the micromixer 10 and thus a rotational motion is created at each of the combine channels 23 and 35. As a result, the ideal layering shown in FIG. 2B can be realized.

Accordingly, the micromixer 10 of the present exemplary embodiment leads to ideal layering without using a split wall. That is, the number of boundary surfaces between two different fluids increases exponentially and thus effective chaotic mixing is realized. Particularly, since no split wall is provided, the micromixer 10 can be inexpensively manufactured through a mass-production process such as an injection molding process. Further, considering that microchannels having a rectangular cross section and manufactured through a normal MEMS process have a characteristic in that a width thereof is significantly greater than a thickness thereof, the micromixer 10 of the present exemplary embodiment induces layering in a direction of a thickness that is relatively thin to thereby effectively reduce a fluid diffusion length. Finally, in the micromixer 10 of the present exemplary embodiment, since the first and second mixing units 20 and 30 allow lengths of the flow passages for the split fluid to be the same, a portion where no mixing occurs can be eliminated.

Figure 3:
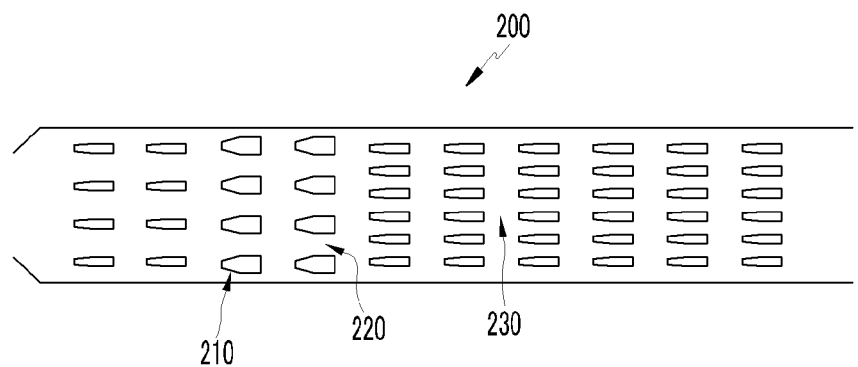
FIG. 3 is a top plan view of a microfilter of a microfluidic biochip for blood typing according to the first exemplary embodiment of the present invention.

The microfilter 170 of the microfluidic biochip for blood typing according to the first exemplary embodiment is illustrated in FIG. 3 by way of example. FIG. 3 shows an initial section 200 of the microfilter 170 of the microfluidic biochip for blood typing according to the present exemplary embodiment.

The microfilter 170 includes a plurality of micropillars 210 arranged in columns and uniformly spaced apart from each other in each of the columns in a direction in which the fluid flows. Filter spaces 220 are formed respectively between pairs of the micropillars 210 of adjacent columns. An inlet of each filter space 220 is larger than an outlet of the same. In the initial section 200, there are steps where the size of the space 220 of each column increases along the fluid flow direction. Also, in the initial section 200, there are steps where the number of micropillars 210 of each column increases along the fluid flow direction. A front surface (i.e., a surface facing the outlet) of each micropillar 210 is larger than a rear surface (i.e., a surface facing the inlet) thereof. That is, a planar cross-section of each micropillar 210 is trapezoidal or pentagonal.

That is, the initial section 200 has multi-step filter spaces 220 and the micropillars 210, each having a planar cross section of an identical trapezoid or pentagonal shape, are patterned in a direction perpendicular to the flow direction of the fluid. Therefore, the filter spaces 220 in a vertical direction are identical to each other. Due to the shape characteristics of the micropillars 210, each having a planar cross-section of an identical trapezoid or pentagonal shape, the inlet of each filter space 220 becomes larger than the outlet thereof. In the fluid flow direction, the micropillars 210, each having a planar cross section of an identical or different trapezoid or pentagonal shape, are arranged in a predetermined pattern. Therefore, the filter spaces 220 having a variety of widths may be arranged in the fluid flow direction. In addition, each of the minimum widths of each of the filter spaces 220 and each of the micropillars 210 may be 50 μm or more in consideration of the fact that red blood cells have a size of 10 μm in a radial direction and in consideration of the injection molding process for mass-production.

As described above, in order to perform accurate blood typing, red cell typing and serum typing should be simultaneously performed, and the typing results should be compared with each other. In this case, for red cell typing, since Anti-A, Anti-B, Anti-AB, Anti-A1, Anti-H, and Anti-D may be used as standard serums that are reagents used for a red blood cell of an identical blood sample, a total of 6 test lines are necessary for each blood typing. Also, for serum typing, since Test cell A1, Test cell A2, Test cell B, and Test cell O may be used as standard red blood cells that are reagents used for a serum of an identical blood sample, a total of 4 test lines are necessary for each blood typing.

Figure 4:
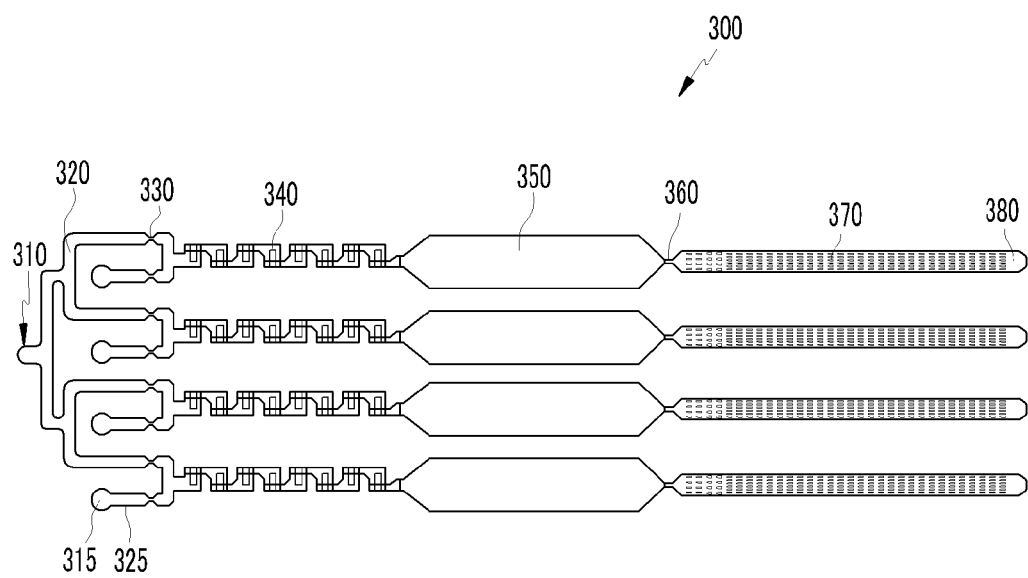
FIG. 4 is a top plan view of a microfluidic biochip for blood typing, which has four typing lines, according to a second exemplary embodiment of the present invention.
Figure 5:
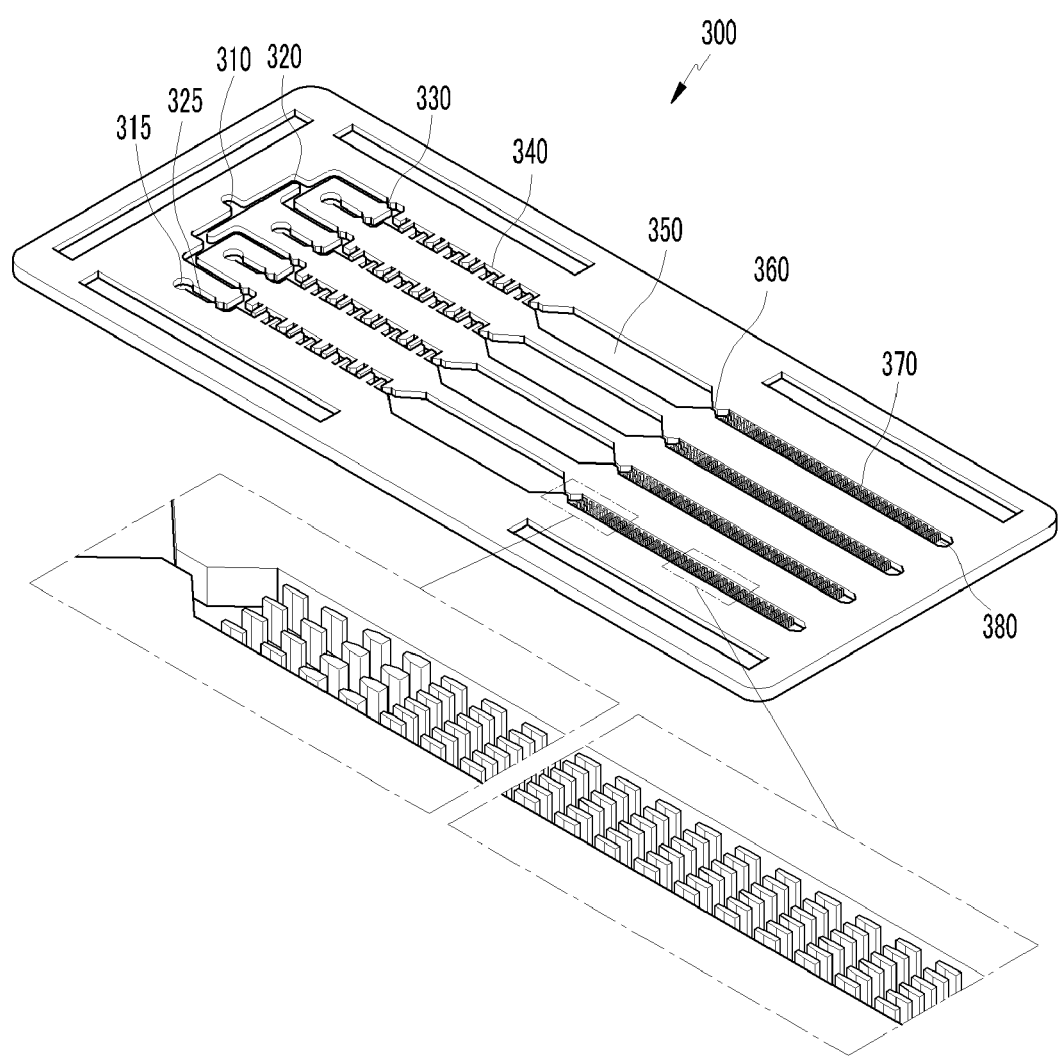
FIG. 5 is a perspective view of a microfluidic biochip for blood typing, which has four typing lines, according to the second exemplary embodiment of the present invention.

FIGS. 4 and 5 are respectively top plan and perspective views of a microfluidic biochip having 4 test lines for simultaneously performing a variety of different forms of blood typing according to a second exemplary embodiment of the present invention.

Referring to FIGS. 4 and 5, a microfluidic biochip 300 for blood typing according to the second exemplary embodiment of the present invention includes a specimen inlet 310, reagent inlets 315, a fluid flow split microchannel 320 that splits the specimen to simultaneously perform a variety of different forms of blood typing, microchannels 325 for transferring the reagent, first passive microvalves 330 for controlling flows of the specimen and the reagent, serpentine lamination chaos micromixers 340 for effectively mixing the specimen with the reagent, reaction microchambers 350 for inducing reaction by storing mixtures of the specimen and the reagent, second passive microvalves 360 for allowing the mixtures of the specimen and the reagent to stay in the reaction microchambers 350, microfilters 370 for filtering off a red blood cell agglutination body formed by the agglutination reaction of the specimen and the reagent that are mixed with each other, and outlets 380 for discharging the specimen and the reagent that are used for blood typing. Each of the test lines has all of the elements (the specimen and reagent inlets, microchannel, first passive microvalve, serpentine lamination micromixer, second passive microchannel, microchannel, and outlet) of the microfluidic microchip of the first exemplary embodiment described with reference to FIG. 1, in addition to the fluid flow split microchannel 320.

The following will briefly describe an operational concept of the microfluidic biochip for blood typing according to the second exemplary embodiment with reference to FIGS. 4 and 5.

Depending on a form of blood typing, 1-3 μl of each of the specimen and the reagents are respectively injected through the specimen inlet 310 and the reagent inlets 315. Since the specimen inlet 310 and the reagent inlets 315 are separately and individually provided, and a plurality of the reagent inlets 315 (4 reagent inlets in this second exemplary embodiment) are provided, a variety of different agglutinogen reaction tests can be simultaneously performed. That is, a variety of different reagents for red cell typing and serum typing particularly can be used in accordance with the purpose of the typing. The injected specimen is directed to the first passive microvalves 330 along each test line after being split through the fluid flow micro channels 320 by a driving force generated by an external pressure transferring device such as a needle pump, by surface tension, by gravity generated and intensified by shaking the chip, or the like. Further, the reagents are directed to the first passive microvalves 330 via the transfer micro channels 325 by the driving force.

The first passive microvalves 330 are shaped such that widths thereof are sharply reduced. This shape leads to a sudden variation in surface tension and thus induces an effect where the flows of the specimen and reagent stop at the first passive microvalves 330. Specifically, the surface tension effect of the first passive microvalves 330 may be enhanced with the surfaces thereof being hydrophobic or hydrophilic according to a plastic surface property. The specimen and reagents stopping at the first passive micro valves 330 are simultaneously directed to the serpentine lamination chaos micromixers 340 by a driving force generated by an external pressure transferring device such as a needle pump, by surface tension, by gravity generated and intensified by shaking the chip, or the like, and are effectively mixed with each other.

Such effective mixture superbly increases blood typing performance and helps to effectively detect an unexpected blood type that may exist in the specimen. Further, the serpentine lamination chaos micromixers 34 are simple in shape which is beneficial for mass-production of the microfluidic biochips for blood typing. A mixture of the specimen and the reagent that are mixed with each other by the serpentine lamination chaos micromixers 340 is further directed to the reaction microchambers 350 by an external pressure transferring device such as a needle pump, surface tension, gravity generated by shaking the chip, or the like.

Like the serpentine lamination chaos micromixers 140, the reaction microchambers 350 are patterned on the upper and lower plates to thereby increase the volume of the chamber. At this point, the mixture of the specimen and reagent is held at the reaction microchambers 350 by the second passive microvalves 360 for a reaction time (about 1-3 minutes) during which the specimen and the regent react each other. If corresponding agglutinogen and agglutinin exist respectively in the specimen and the reagent, the agglutination reaction occurs between the red blood cells.

Like the first passive microvalves 330, the second passive microvalves 360 are also shaped such that widths thereof are sharply reduced. This shape leads to a sudden variation in surface tension and thus induces an effect where the flow of the mixture of the specimen and reagent stops at the second passive microvalves 360. Specifically, the surface tension effect of the second passive microvalves 360 may be enhanced as the surfaces thereof are formed to be hydrophobic or hydrophilic according to a plastic surface property. After a predetermined reaction time (about 1-3 minutes) during which the specimen and the regent react with each other has elapsed, the mixture of the specimen and the regent is directed to the microfilters 370 by an external pressure transferring device such as a needle pump, surface tension, gravity generated by shaking the chip, or the like.

The microfilter 370 applied to the microfluidic biochip 100 for blood typing of the present exemplary embodiment has a filter space that is reduced in multiple steps to effectively filter the agglutinated red blood cells for which the agglutination reaction is induced. Specifically, the filter space is larger than a size of each of the normal red blood cells and thus the red blood cells for which no agglutination reaction occurs can easily pass through the microfilters 370. However, the agglutinated red blood cells whose size increases due to the agglutination reaction are easily filtered off by the microfilters 370.

Finally, the specimen and the reagent that react with each other for a predetermined reaction time pass through the microfilters 370 and are discharged through the outlets 380. At this point, when the agglutination reaction occurs between the specimen and the reagent, the agglutinated red blood cells are filtered off by the microfilters 370. When no agglutination reaction occurs, the red blood cells pass through the microfilters 370 and thus are easily identified by the naked eye if the agglutination occurs. Particularly, in the case of the microfluidic biochip 300 for blood typing of FIGS. 4 and 5, four types of typing can be simultaneously performed, based on which the blood typing is enabled.

The following will describe a process for manufacturing a microfluidic biochip for blood typing according to an exemplary embodiment of the present invention with reference to FIGS. 6A to 6K. In the description of the present exemplary embodiment, if it is determined that the detailed description on the technology well-known in the art and the constitution may unnecessarily cloud the concept of the present invention, the detailed description thereof will be omitted herein. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Therefore, the concept of the present invention should be construed based on the overall description of this specification.

FIGS. 6A to 6K are process views sequentially illustrating processes for manufacturing the microfluidic biochip for blood typing, particularly through mass-production using injection molding, according to an exemplary embodiment of the present invention.

Figure 6A:
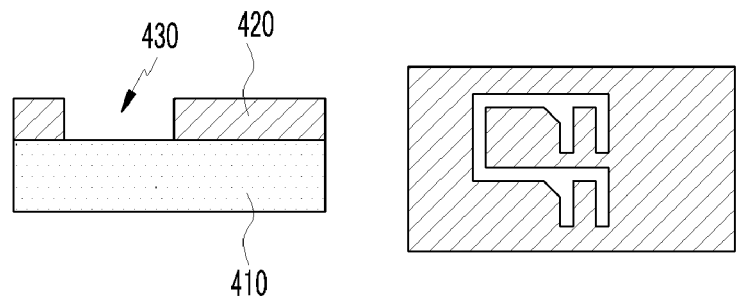
FIGS. 6A to 6K are views illustrating sequential processes for manufacturing a microfluidic biochip, specifically, sequential processes for a mass-production process using injection molding.

First, FIGS. 6A to 6 sequentially show processes for manufacturing an upper plate of the microfluidic biochip according to the present exemplary embodiment.

First, a substrate (e.g., a nickel metal substrate) 410 is washed through a surface washing process and, as shown in FIG. 5A, a photoresist 420 such as SU-8 is deposited on the substrate to form a first groove 430 having a shape corresponding to all of the specimen inlet, the reagent inlet, the specimen fluid flow split microchannels, the reagent transfer microchannels, the first passive microvalves, the F-shaped mixture unit of the serpentine lamination chaos micromixer, the reaction microchamber, the second passive microvalves, the microfilter, and the outlet, through conventional ultraviolet ray photolithography.

Figure 6B:
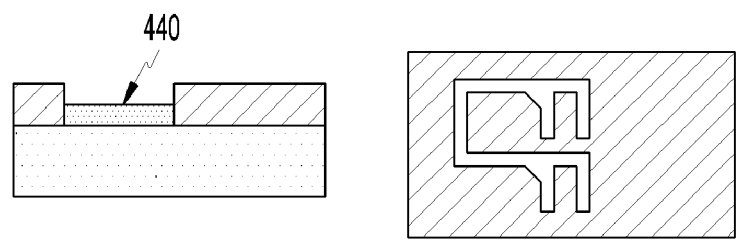

Next, as shown in FIG. 6B, a metal 440 such as copper or nickel is formed on the first groove 430 having the shape corresponding to all of the specimen inlet, the reagent inlet, the specimen fluid flow split microchannels, the reagent transfer microchannels, the first passive microvalves, the F-shaped mixture unit of the serpentine lamination chaos micromixer, the reaction microchamber, the second passive microvalves, the microfilter, and the outlet, through electroplating or electroforming.

Figure 6C:
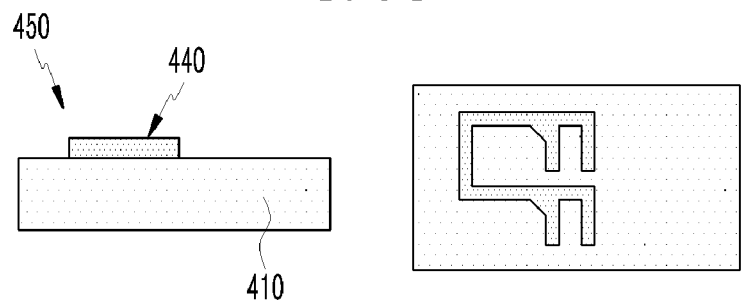

Next, when the photoresist 420 such as the SU-8 formed as shown in FIG. 6C is removed through, for example, an etching process, a mold insert 450 used for manufacturing the upper plate of the microfluidic biochip for blood typing is prepared.

Figure 6D:
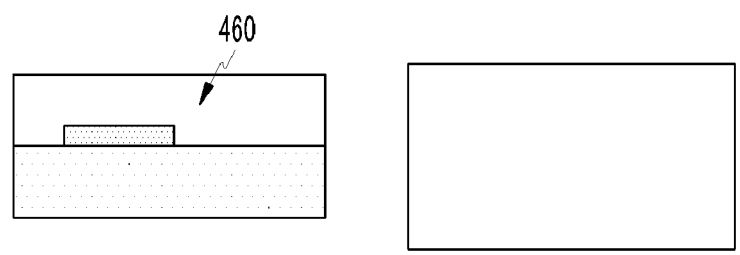

Subsequently, as shown in FIG. 6D, a polymer 460 such as COC (cyclic olefin copolymer), PMMA (polymethylmethacrylate), PS (polystyrene), PC (polycarbonate), PDMS (polydimethylsiloxane), Teflon (Polytetrafluoroethylene), and PVC (polyvinylchloride) is molded through a mass-production process such as injection molding, hot embossing, UV-molding, and casting.

Figure 6E:
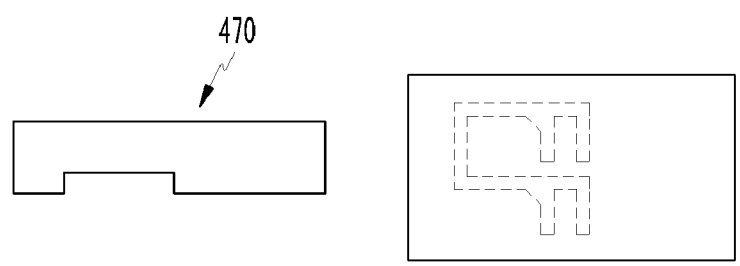
Figure 6F:
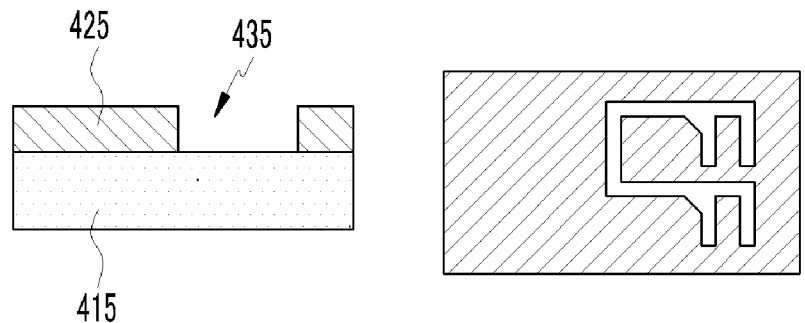

Next, as shown in FIG. 6E, when the molded polymer 460 is ejected, an upper plate 470 of the microfluidic biochip for blood typing is obtained.

FIGS. 6F to 6J sequentially show processes for manufacturing a lower plate of the microfluidic biochip for blood typing according to an exemplary embodiment of the present invention.

First, a substrate (e.g., a nickel metal substrate) 415 is washed through a surface washing process and, as shown in FIG. 6A, a photoresist 425 such as SU-8 is deposited on the substrate to form a second space corresponding to the F-shaped mixture unit of the serpentine lamination chaos micromixer and the reaction microchamber through conventional ultraviolet ray photolithography.

Figure 6G:
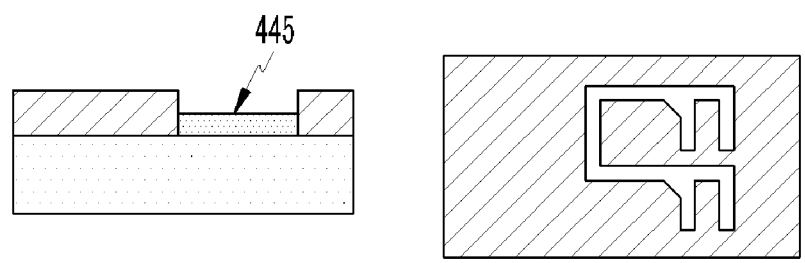

Next, as shown in FIG. 6G, a metal 445 such as copper or nickel is formed on the second groove 435 having a shape corresponding to the F-shaped mixture unit of the serpentine lamination chaos micromixer and the reaction microchamber through electroplating or electroforming.

Figure 6H:
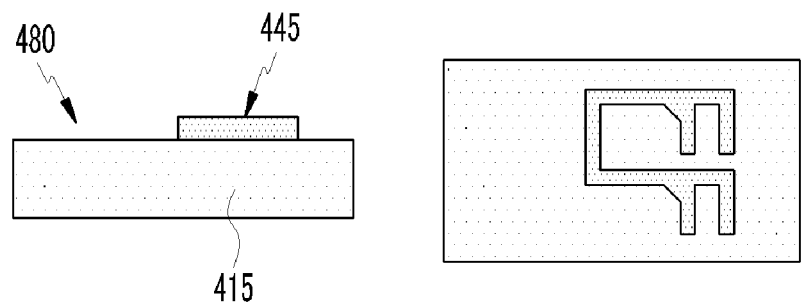

Subsequently, when the photoresist 425 such as the SU-8 formed as shown in FIG. 6H is removed through, for example, an etching process, a mold insert 480 used for manufacturing the lower plate of the microfluidic biochip for blood typing according to the present exemplary embodiment is prepared.

Figure 6I:
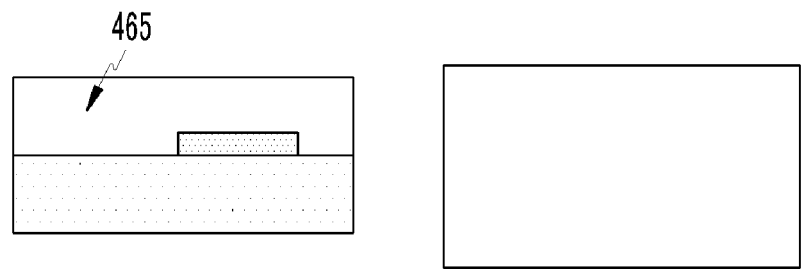
Figure 6J:
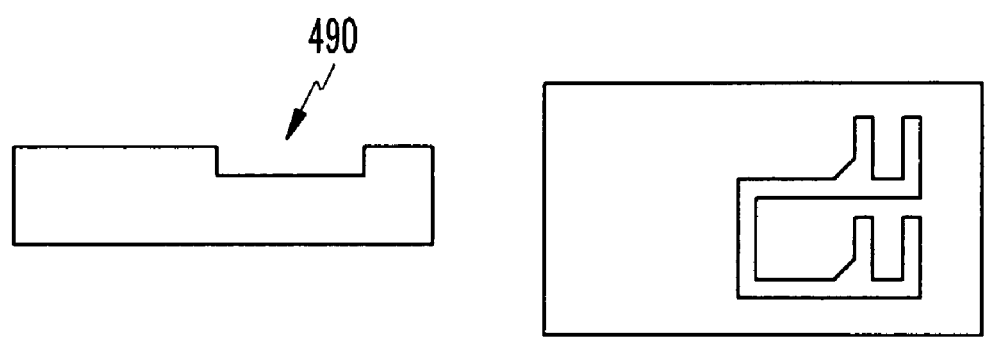

Subsequently, as shown in FIG. 6I, a polymer 465 such as COC (cyclic olefin copolymer), PMMA (polymethylmethacrylate), PS (polystyrene), PC (polycarbonate), PDMS (polydimethylsiloxane), Teflon (Polytetrafluoroethylene), and PVC (polyvinylchloride) is molded through a mass-production process such as injection molding, hot embossing, UV-molding, and casting. Next, as shown in FIG. 6J, when the molded polymer 465 is ejected, a lower plate 490 of the microfluidic biochip for blood typing according to the present exemplary embodiment is obtained.

Figure 6K:
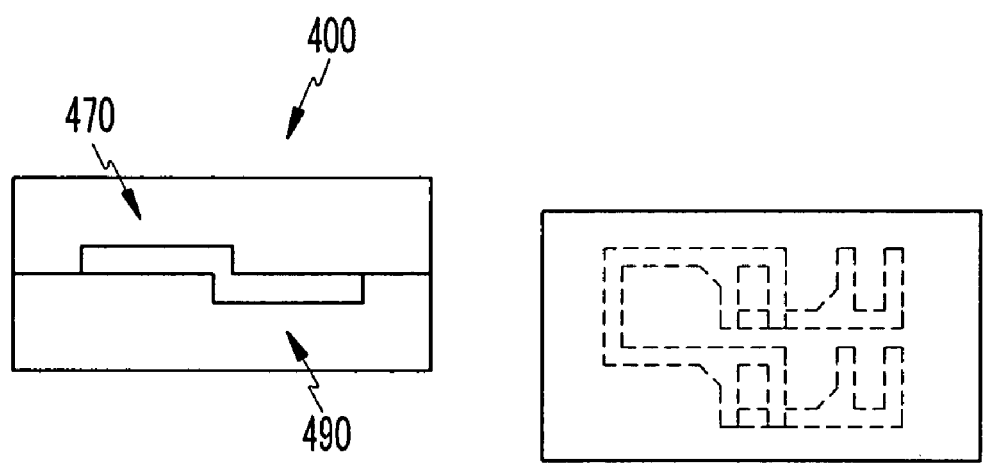

Finally, as shown in FIG. 6K, the upper plate 470 and the lower plate 490 are bonded together through a bonding method selected from the group consisting of thermal bonding, bonding using a bonding material, lamination bonding, and ultrasonic wave bonding, thereby completing the microfluidic biochip 400 for blood typing.

Briefly describing the method, the mold inserts 450 and 480 used for manufacturing the microfluidic biochip 400 for blood typing according to the present exemplary embodiment are prepared through the processes illustrated in FIGS. 6C to 6H and the upper and lower plates 470 and 490 for the microfluidic biochip 400 for blood typing according to the present exemplary embodiment are prepared through the processes illustrated in FIGS. 6E to 6I. Finally, as shown in FIG. 6K, the upper plate 470 and the lower plate 490 are bonded together, thereby completing the microfluidic biochip 400 for blood typing.

However, a method of manufacturing the microfluidic biochip of the present invention is not limited to the above-described method. For example, the microfluidic biochip for blood typing of the present invention may be directly formed of a polymer through a milling or forming process. In addition, the specimen inlet, the reagent inlet, the specimen fluid flow split microchannels, the reagent transfer microchannels, the first passive microvalves, the F-shaped mixture unit of the serpentine lamination chaos micromixer, the reaction microchamber, the second passive microvalves, the microfilter, and the outlet space of the microfluidic biochip can be formed through a patterning process using a photoresist or directly etching a silicon substrate without using the molding technique. It is also possible for a photoresist patterned on a substrate to be directly used as the molding insert.

The following will describe results of blood typing test performed using the fluidic biochip having the above-described concept and manufactured in accordance with the above-described method.

Figure 7:
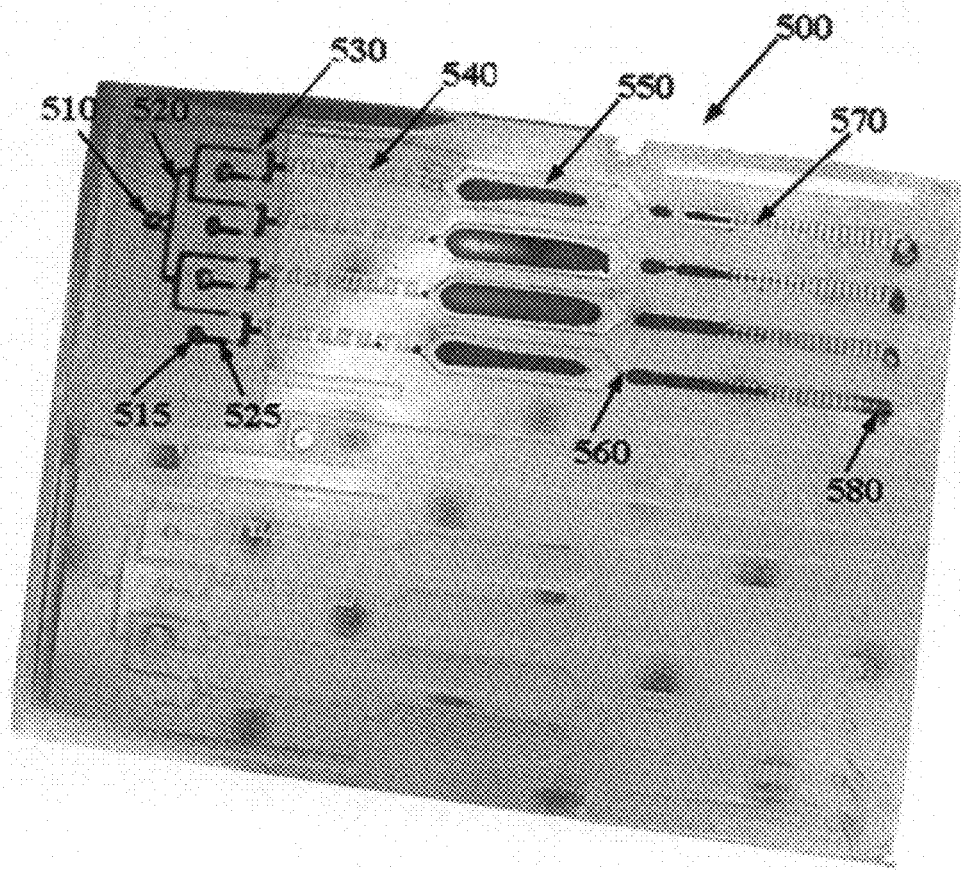
FIG. 7 is a picture showing an actual microfluidic biochip for blood typing, which has been manufactured through an injection molding process and a thermal-bonding process according to an exemplary embodiment of the present invention.

FIG. 7 is a picture showing a microfluidic biochip for blood typing, which is actually manufactured through an injection molding process and a thermal-bonding process in accordance with one embodiment of the present invention.

Referring to FIG. 7, the actual microfluidic biochip 500 has two basic units of the second embodiment shown in FIG. 3. That is, the actual microfluidic biochip 500 is configured to simultaneously perform the red cell typing and the serum typing for one blood sample (one blood typing).

The microfluidic biochip for blood typing, which is shown in FIG. 7, includes a specimen inlet 510, reagent inlets 515, a fluid flow split microchannel 520 that splits the specimen to simultaneously perform a variety of different blood typing, microchannels 525 for transferring the reagent, first passive microvalves 530 for controlling flows of the specimen and the reagent, serpentine lamination chaos micromixers 540 for effectively mixing the specimen with the reagent, reaction microchambers 550 for inducing a reaction by storing the mixture of the specimen and the reagent, second passive microvalves 560 for allowing the mixture of the specimen and the reagent to stay in the reaction microchambers 550, microfilters 570 for filtering off a red blood cell agglutination body formed by the agglutination reaction of the specimen and the reagent that are mixed with each other, and outlets 580 for discharging the specimen and the reagent that are used for the blood typing.

Figure 8A:
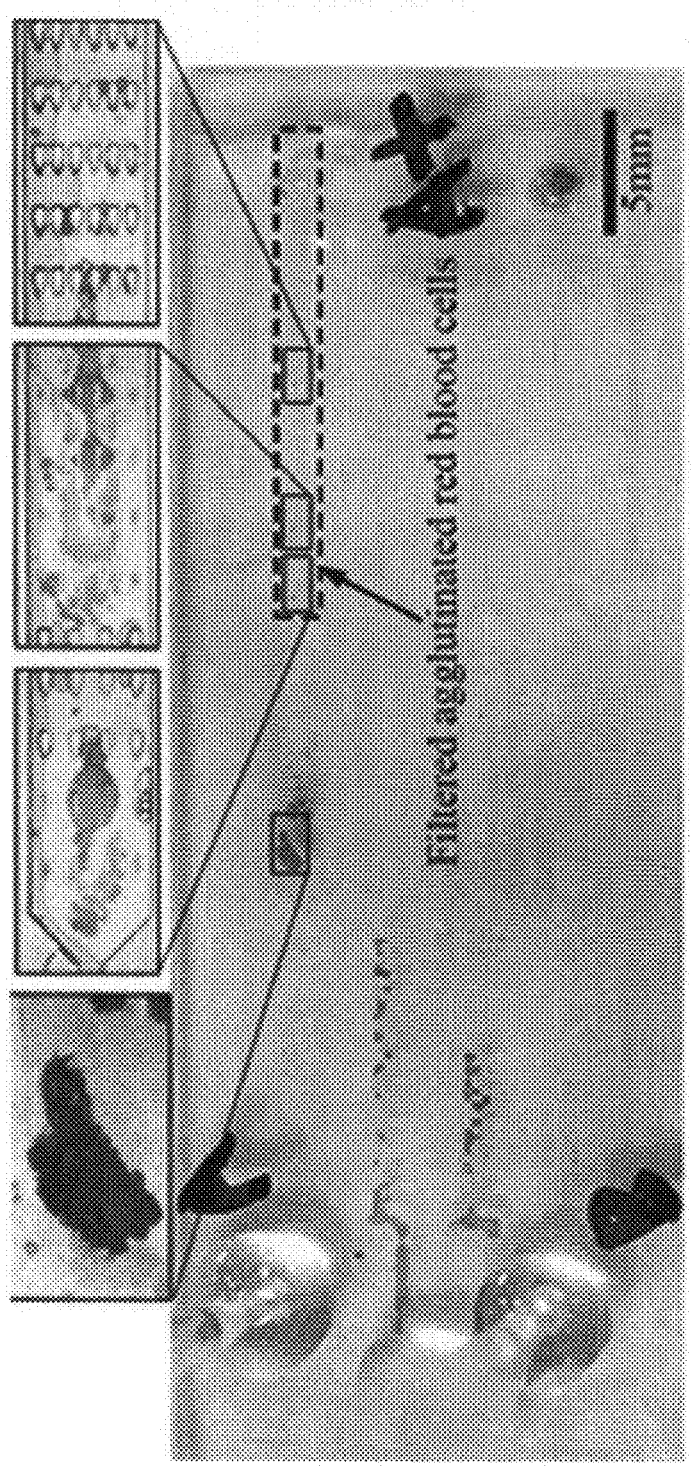
FIGS. 8A to 8C are pictures showing blood typing results that are obtained by performing blood typing using actual microfluidic biochips that have been manufactured through an injection molding process and a thermal-bonding process according to an exemplary embodiment of the present invention.
Figure 8B:
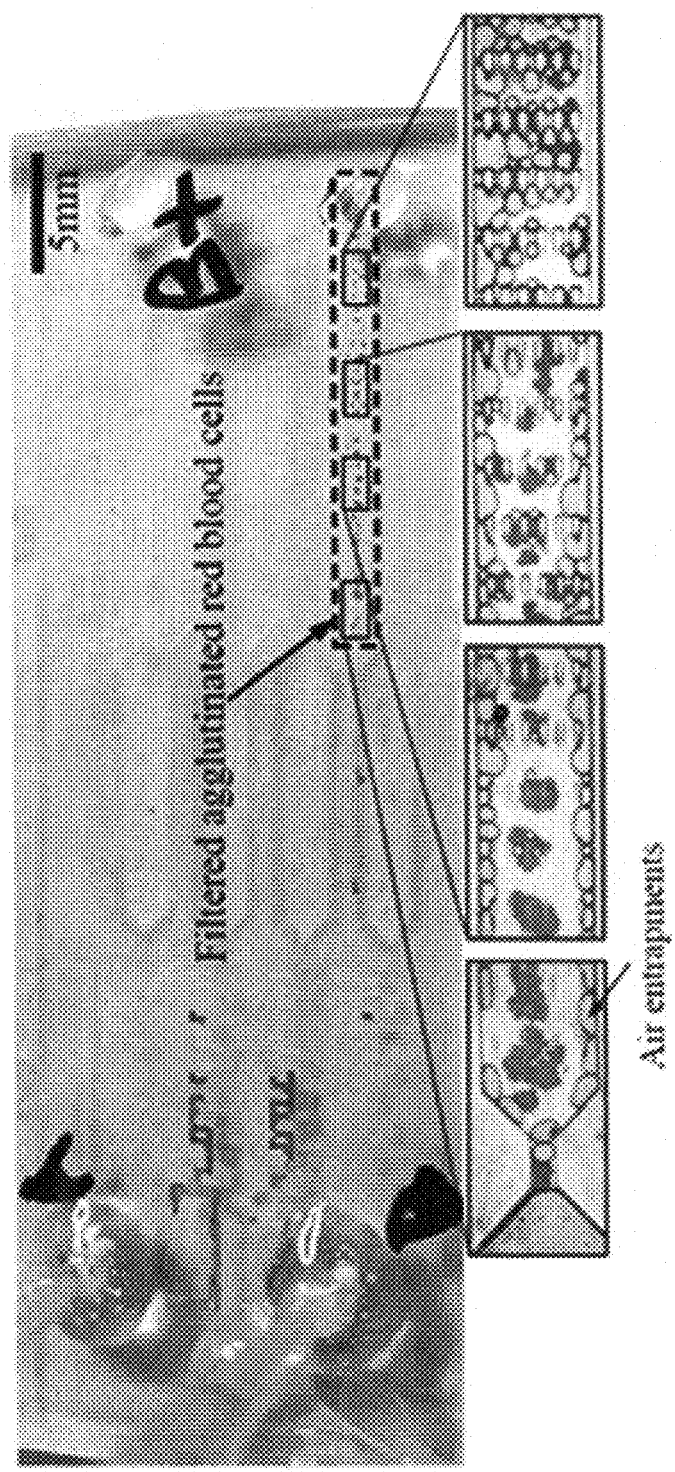
Figure 8C:
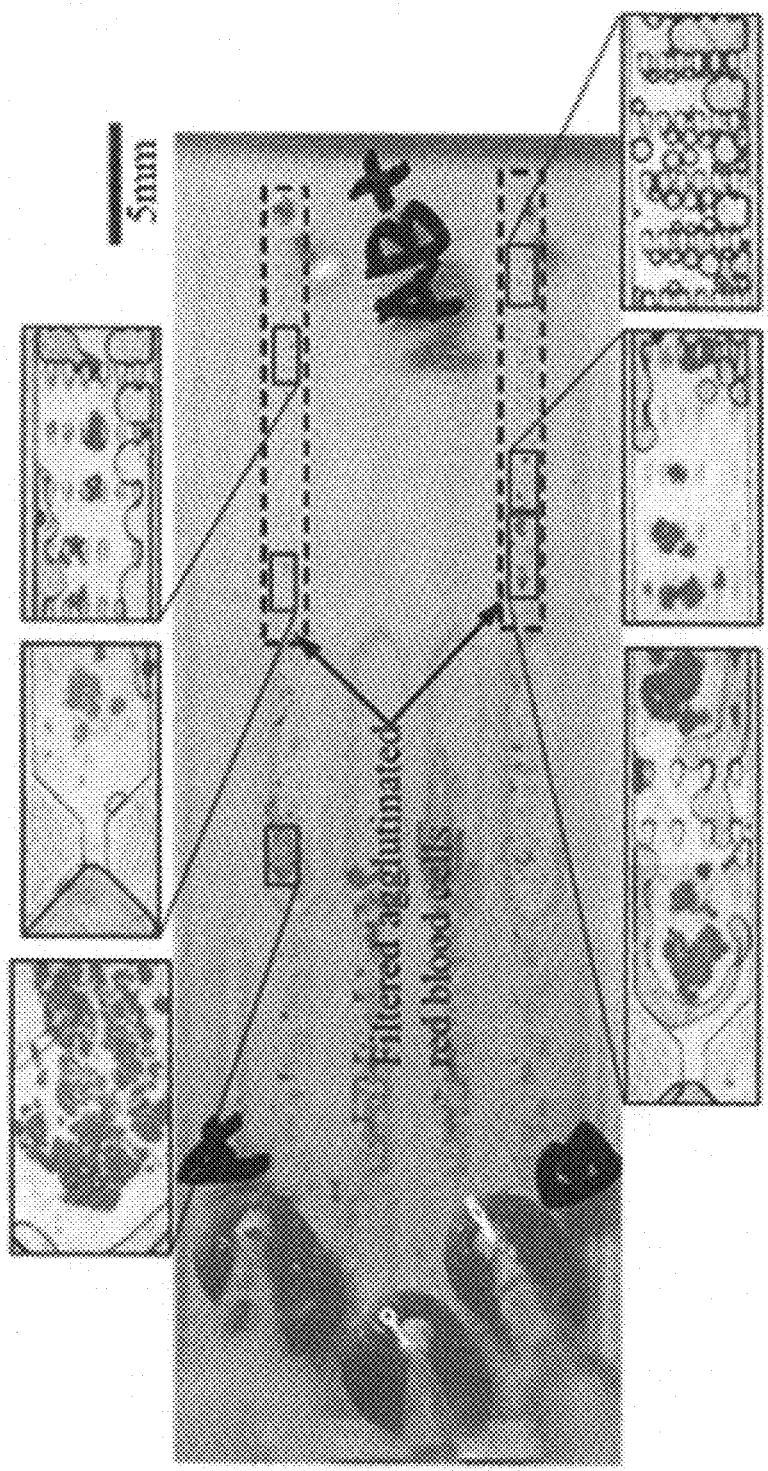

FIGS. 8A to 8C show results of blood typing tests performed using the fluidic biochip that is actually manufactured through an injection molding process and a thermal-bonding process in accordance with one embodiment of the present invention. Particularly, FIG. 8A shows a test result for blood type-A, FIG. 8B shows a result for blood type-B, and FIG. 8C shows a test result for blood type-AB.

A specimen of actual red blood cells was injected through a specimen inlet and reagents of Anti-A and Anti-B were injected through the reagent inlets. The injected specimen of the red blood cells was mixed with the reagents of Anti-A and Anti-B through the serpentine lamination chaos micromixer. The specimen and reagents that are mixed with each other reacted with each other in each reaction microchamber and passed through the microfilters.

Blood type-A can be identified in that the agglutinated red blood cells are filtered off by the microfilter of the test line, in which the reagent of Anti-A is injected, as shown in FIG. 8A. Further, for blood type-B, it can be identified that the agglutinated red blood cells are filtered off by the microfilter of the test line, in which the reagent of Anti-B is injected, as shown in FIG. 8B. In addition, for blood type-AB, it can be identified that the agglutinated red blood cells are filtered off by the microfilters of the test lines, in which the reagents of Anti-A and Anti-B are injected, as shown in FIG. 8B. Through the above tests, it was identified that the blood typing can be successfully performed by the microfluidic biochip according to the embodiment of the present invention.

Although the present invention is described with reference to the practical embodiments, the present invention should not be construed as being limited to the embodiments; rather these embodiments are provided so that this disclosure will be throughout and complete, and will fully convey the concept of the invention to those skilled in the art. Rather, it should be clearly understood that many variations and/or modifications of the basic inventive concept taught herein still fall within the spirit and scope of the present invention.

According to the above-described microfluidic biochip of the present invention, by realizing the specimen inlet, the reagent inlet, the split microchannel, the transfer microchannels, the chaos micromixer, the reaction microchamber, the microfilter, the passive microvalve, and the outlet on a plastic chip, the blood typing based on the agglutination reaction that is frequently used as qualitative typing in the diagnosis medicine can be simply but accurately and objectively performed at any place.

When the microfluidic biochip for blood typing according to the present invention is used, the blood cell typing and the serum typing can be simultaneously performed and thus the accuracy and objectivity of the blood typing can be improved by crossmatching the results of the two forms of the typing. Further, since the inlets for the specimen and the reagents are separated from each other, a variety of agglutination reaction tests can be performed using a variety of reagents. In addition, since the specimen is split through the split microchannels, a variety of forms of blood typing can be simultaneously performed.

Particularly, the serpentine lamination chaos micromixer applied to the microfluidic biochip for blood typing of the present invention promotes the agglutination reaction by effectively mixing the specimen and the reagent, thereby enhancing the accuracy of the blood typing and enabling the detection of the unexpected blood type that may exist in the blood cells of the specimen. The first passive microvalve allows the specimen and the reagent to be simultaneously introduced into the micromixer and the second passive microvalve allows the mixture of the specimen and the reagent to stay in the reaction microchamber for a reaction time. Finally, the microfilter having multi-step spaces defined by a plurality of trapezoid micropillars effectively filters off agglutinated blood cells, thereby improving the efficiency of the blood typing.

Further, since the shapes of the specimen inlet, the reagent inlet, the split microchannel, the transfer microchannel, the chaos micromixer, the reaction microchamber, the microfilter, the passive microvalve, and the outlet, which are applied to the microfluidic biochip for blood typing of the present invention are simple, the microfluidic biochip can be cheaply made through a mass-production process and thus the products is comparatively inexpensive.

The microfluidic biochip for blood typing of the present invention may be applied to a variety of clinical medicine fields based on the agglutination test.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A microfluidic biochip for blood typing based on an agglutination reaction, comprising:
   a specimen transfer microchannel provided with a specimen inlet;
   one or more reagent transfer microchannels each provided with a reagent inlet;
   one or more micromixers for mixing a specimen and a reagent, which are flowing along thereof, with each other, the micromixer being connected to downstream ends of the specimen and reagent transfer microchannels;
   a first passive microvalve for controlling a flow of the specimen and the reagent, the first passive microvalve being formed between the downstream ends of the specimen and reagent transfer microchannels and an upstream end of the micromixer;
   a reaction microchamber for inducing a reaction between the specimen and the reagent that are mixed with each other and stored therein, the reaction microchamber being connected to a downstream end of the micromixer;
   a microfilter for filtering off an agglutination body resulting from the agglutination reaction between the specimen and the reagent, the microfilter being connected to a downstream end of the microchamber;
   a second passive microvalve for controlling the specimen and the reagent that are mixed with each other to stay at the reaction microchamber, the second passive microvalve being formed between the downstream end of the microchamber and an upstream end of the microfilter; and
   an outlet for discharging the specimen and the reagent that are used for the blood typing, the outlet being connected to a downstream end of the microfilter,
   wherein the microfilter includes a plurality of micropillars arranged in a plurality of columns arranged at periodic intervals in a direction in which fluid flows and filter spaces formed respectively between pairs of the micropillars of adjacent columns,
   wherein each of the micropillars has a surface that is located at a downstream side with respect to the fluid flow direction and that is larger than a surface that is located at an upstream side with respect to the fluid flow direction.

2. The microfluidic biochip of claim 1, wherein each of the filter spaces has an inlet that is wider than an outlet thereof.

3. The microfluidic biochip of claim 1, wherein the columns in which the micropillars are arranged to be uniformly spaced apart from each other.

4. The microfluidic biochip of claim 1, wherein an initial section of the microfilter has sections where the filter spaces of the columns are reduced in multiple steps in a fluid flow direction.

5. The microfluidic biochip of claim 4, wherein the initial section of the microfilter has sections where sizes of the micropillars of the columns increase in multiple steps.

6. The microfluidic biochip of claim 4, wherein the initial section of the microfilter has sections where the number of micropillars in the columns increases in multiple steps.

7. The microfluidic biochip of claim 1, wherein a planar cross-section of each of the micropillars is formed in a trapezoidal shape or a pentagonal shape.

8. The microfluidic biochip of claim 1, wherein the first passive microvalve is shaped such that a width thereof is sharply reduced from the reagent transfer microchannel or the specimen transfer microchannel.

9. The microfluidic biochip of claim 1, wherein the second passive microvalve is shaped such that a width thereof is sharply reduced from the reaction microchamber.

10. The microfluidic biochip of claim 1, wherein a plurality of passages are branched off from the specimen transfer microchannel and are respectively connected to the micromixers to split the injected specimen and transfer the split specimens to the micromixers.

11. The microfluidic biochip of claim 10, wherein the reagent transfer microchannels are respectively connected to the micromixers, each of the reagent transfer microchannels being provided with an independent reagent inlet so that different types of reagents can be injected through the independent reagent inlets.

12. The microfluidic biochip of claim 1, wherein the micromixer transfers the specimen and the reagent through a three-dimensional serpentine passage such that the specimen and the reagent are mixed with each other by a combination of a split/recombine chaotic mixture mechanism and a chaotic mixture mechanism of chaotic advection.

13. The microfluidic biochip of claim 12, wherein the micromixer comprises:
   an inflow channel through which the specimen and the reagent are joined together, the inflow channel being provided with a pair of inlets through which the specimen and the reagent are respectively injected;
   an outflow channel through which the specimen and the reagent are mixed with each other and discharged; and
   first and second mixing units that are disposed in a row and connected between the inflow and outflow channels to mix the specimen and the reagent with each other.

14. The microfluidic biochip of claim 13, wherein:
   the first mixing unit includes a pair of first split channels branched off from the inflow channel and a first combine channel communicating with each end of the first split channels, the first split channels extending toward a first side with respect to a fluid flow direction in the inflow channel so that the mixture fluid of the specimen and the reagent that are combined with each other at the inflow channel is split again and passes therethrough, the first combine channel being disposed on a different layer from the first split channels;

the second mixing unit includes a pair of split channels branched off from the first combine channel and a second combine channel communicating with each end of the second split channels, the second combine channel being disposed on a different layer from the second split channels, the mixture fluids split through the second split channels being combined and passing through the second combine channel; and the second combine channel extends to the discharge channel.

15. The microfluidic biochip of claim 14, wherein each of the first split channels is divided into a main channel extending parallel to the inflow channel and a branch channel extending from the main channel toward the first side in a direction substantially perpendicular to the fluid flow direction in the main channel.

16. The microfluidic biochip of claim 14, wherein each of the second split channels includes a main channel extending parallel to the inflow channel and a branch channel extending from the main channel toward a second side in a direction substantially perpendicular to the fluid flow direction in the main channel.

17. The microfluidic biochip of claim 14, wherein the first and second mixing units that are disposed in a row are repeated several times.

18. The microfluidic biochip of claim 14, wherein the first split channels of the first mixing unit are formed on a different layer from the second split channels of the second mixing unit, and the first combine channel of the first mixing unit is formed on a different layer from the second combine channel of the second mixing unit.

19. The microfluidic biochip of claim 14, wherein the first combine channel is formed on the same layer as the second split channels.

20. The microfluidic biochip of claim 14, wherein the first and second split channels and the first and second combine channels are formed such that the mixture fluid split through each of the split channels can move by a substantially identical distance while the mixture fluid is transferred to a recombine point through each of the combine channels.

21. The microfluidic biochip of claim 1, wherein the specimen is red blood cells of a blood sample and the reagent is a standard serum.

22. The microfluidic biochip of claim 1, wherein the specimen is a serum of a blood sample and the reagent is standard red blood cells.

23. A method of manufacturing the microfluidic biochip as claimed in claim 1, the method comprising;

preparing a substrate including a first groove having a shape corresponding to all of the specimen and reagent channels, a first layer portion of the micromixer, the first and second passive microvalves, a first layer portion of the reaction microchamber, and the microfilter;

preparing a second substrate including a second groove having a shape corresponding to a second layer portion of the micromixer and a second layer portion of the reaction microchamber; and bonding the first and second substrates together.

24. The method of claim 23, wherein the bonding of the first and second substrates is realized through a process selected from the group consisting of thermal bonding, bonding using a bonding material, lamination bonding, and ultrasonic wave bonding.

25. The method of claim 23, wherein the preparing of each of the first and second substrates comprises:

preparing a mold insert corresponding to the first groove or the second groove;

molding a polymer in the mold insert; and ejecting the molded polymer.

26. The method of claim 25, wherein the preparing of the mold insert comprises:

depositing a photoresist on the substrate;

forming the first or second groove through photolithography;

applying a metal in the first or second groove; and removing the photoresist from the substrate.

27. The method of claim 26, wherein the forming of the first or second groove is realized through electroplating or electroforming.

28. The method of claim 25, wherein the molding of the polymer is realized through one of injection molding, hot embossing, UV-molding, and casting.

29. The method of claim 25, wherein the polymer is a thermoplastic polymer resin or a thermosetting polymer resin.

30. The method of claim 25, wherein the polymer is selected from the group consisting of a COC (cyclic olefin copolymer), PMMA (polymethylmethacrylate), PS (polystyrene), PC (polycarbonate), PDMS (polydimethylsiloxane), Teflon (Polytetrafluoroethylene), and PVC (polyvinylchloride).

31. The method of claim 25, wherein the preparing of the mold insert is realized through a micromilling process.

32. The method of claim 25, wherein the preparing of the mold insert is realized by patterning a photoresist on the substrate.

33. The method of claim 23, wherein the preparing of each of the first and second substrates is realized by directly shaping the first or second groove on a polymer or a metal through a precise forming process.

34. The method of claim 23, wherein the preparing of each of the first and second substrates is realized by directly etching the substrate to form a pattern corresponding to the first or second groove.

* * * * *